United States Patent
Hoheisel

(10) Patent No.: US 7,940,889 B2
(45) Date of Patent: May 10, 2011

(54) MAMMOGRAPHY METHOD AND APPARATUS WITH IMAGE DATA OBTAINED AT DIFFERENT DEGREES OF BREAST COMPRESSION

(75) Inventor: Martin Hoheisel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/428,785

(22) Filed: Apr. 23, 2009

(65) Prior Publication Data

US 2009/0268866 A1    Oct. 29, 2009

(30) Foreign Application Priority Data

Apr. 24, 2008   (DE) .................... 10 2008 020 670

(51) Int. Cl.
*A61B 6/04* (2006.01)
(52) U.S. Cl. ......................................................... 378/37
(58) Field of Classification Search ............... 378/37
See application file for complete search history.

(56) References Cited

U.S. PATENT DOCUMENTS

| | | | |
|---|---|---|---|
| 6,049,583 A | | 4/2000 | Galkin |
| 6,647,089 B1 * | | 11/2003 | Virta et al. ...................... 378/37 |
| 6,833,703 B2 | | 12/2004 | Sinkus et al. |
| 7,025,253 B2 | | 4/2006 | Sinkus et al. |
| 2004/0094167 A1 * | | 5/2004 | Brady et al. .................. 128/916 |
| 2004/0234113 A1 | | 11/2004 | Miga |
| 2006/0098855 A1 | | 5/2006 | Gkanatsios et al. |
| 2006/0269040 A1 | | 11/2006 | Mertelmeier |
| 2007/0238966 A1 | | 10/2007 | Sun et al. |
| 2009/0149750 A1 | | 6/2009 | Matsumura |

FOREIGN PATENT DOCUMENTS

FR   2733142   10/1996

OTHER PUBLICATIONS

"Lung Strain Profiles Using Computed Tomography Elastography," Fredman et al, Proc. 26th Annual Int. Conf. Of IEEE EMBS (2004) pp. 1545-1548.

* cited by examiner

*Primary Examiner* — Chih-Cheng G Kao
(74) *Attorney, Agent, or Firm* — Schiff Hardin LLP

(57) ABSTRACT

In a method and apparatus to generate a mammographic image, the apparatus has a radiation source, a digital radiation detector, and support plate and a compression plate between which the breast is compressed during image acquisition. A first image data set depicting the breast is acquired, with a first degree of compression of the breast. A second degree of compression of the breast is set and a second image data set depicting the breast is acquired. The first and second image data sets are linked for the generation of the diagnostic image.

16 Claims, 2 Drawing Sheets

MAMMOGRAPHY METHOD AND APPARATUS WITH IMAGE DATA OBTAINED AT DIFFERENT DEGREES OF BREAST COMPRESSION

BACKGROUND OF THE INVENTION

1. Field of the Invention

The present invention concerns a method to generate an image with a mammography apparatus of the type having a radiation source, a digital radiation detector, and a support plate and a compression plate between which the breast is compressed during acquisition of an image.

2. Description of the Prior Art

The most successful method for the examination of the female breast to determine possible suspicious lesions is mammography, either in the framework of a screening independent of suspicion or given an already present suspicion of breast cancer. For this purpose, it is known to use a mammography apparatus having an x-ray source and a digital radiation source as well as a support plate and a compression plate between which the breast is placed while the image is acquired, the breast being compressed by the vertically adjustable compression plate. The breast is located between the radiation source and the digital radiation detector so that a radiation image of the breast can be acquired. The sensitivity of the method is high. An additional clarification by extraction of a biopsy sample (thus a surgical procedure) typically ensues if a suspicious region in the acquired mammography image is detected. Not only is this a problematic stress for the patient, but also a significant cost is incurred. In order to improve the specificity of the diagnosis using the mammography image, and in order to differentiate a benign lesion from a malignant lesion, in cases of doubt various different methods are frequently used, for example ultrasound examinations, and optical radioscopy or a magnetic resonance examination. However, these methods likewise have disadvantages. Ultrasound examinations are time-consuming and must be conducted by the physician himself or herself. Optical radioscopy is less established as a method and not sufficiently specific, while magnetic resonance examinations are very cost-intensive and time-intensive.

SUMMARY OF THE INVENTION

An object of the present invention is to provide a method for the generation of a mammography image that enables a higher degree of specificity relative to a simple mammography image acquisition.

This object is achieved by a method of the aforementioned general type with the following steps in accordance with the invention: acquisition of a first image data set depicting the breast, with a first degree of compression of the mamma, adjustment of a second degree of compression of the breast and acquisition of a second image data set depicting the breast, and computational linking of the first and second image data sets for the generation of the image.

The method according to the invention integrates elastography into the method of mammography. In the method according to the invention, two separate image data sets of respective images of the compressed breast are acquired, wherein the breast is compressed to different degrees (consequently is deformed). The variation of the degree of compression of the first image from the second image inevitably occurs as a consequence of geometric tissue variation, meaning that the tissue—starting from the given geometry for the tissue distribution during the first image exposure—varies in terms of position; it shifts in space due to the compression change. After setting the second degree of compression, a second image is acquired. These two images are subsequently computationally combined with one another in order to generate a final image that then can be output on a monitor, possibly together with the two acquired individual images.

Elastography is based on the fact that the elastic response of different tissue structures is different. Soft, healthy tissue moves differently than hard, pathological tissue given exertion of a pressure on the tissue. The method according to the invention is based on the recognition that a benign lesion behaves differently (viewed elastographically)—consequently moves differently in space given a pressure application—than a malignant lesion (thus a cancerous tissue). As long as the breast thus represents an essentially homogenous, plastic tissue, the deformation essentially ensues uniformly, and existing tissue parts, glands, lipomas, etc. essentially shift uniformly and homogenously in space. By contrast, malignant lesions are significantly less deformable, such that they shift and deform in an abnormal manner in the homogenous tissue surrounding them. This difference resulting from the different elasticity is utilized in the method according to the invention by the two images or image data sets being acquired at different breast compressions and being computationally combined with one another in order to generate the diagnostic image to be evaluated and output. In this image, image information resulting from the different elasticity behavior (thus from elastography) can be extracted and diagnostically evaluated due to the computational link, meaning that a possible malignant lesion can be detected significantly more precisely than using only a single mammography radioscopy acquisition.

The method according to the invention thus combines the high sensitivity of x-ray radioscopic mammography with the advantages of an elastography, and the specificity of the method strikingly improves because not only mammographic information but also elastographic information influence the computationally generated final image to be output.

In an embodiment of the invention, one of the two image data sets is transformed before the linking, based on the assumption of a homogenous elastic behavior of the breast, such that the elastic variation of the imaged breast resulting from the variation of the degree of compression is compensated. A computational compensation of the average, uniform deformation of the breast that ensues from the variation of the degree of compression thus is achieved. For example, the second acquired image or the second acquired image data set is transformed by this retrograde calculation so that the transformed image is approximately based on the same degree of compression as the first acquired image or image data set. As a result, the summary expansion of the breast in the transformed second image data set or second image is equal to the expansion of the breast in the untreated first image or first image data set; both are thus made equally large. As described above, this retrograde calculation assumes an essentially homogenous elasticity behavior of the entirety of the breast tissue in order to computationally transform the individual pixels in the retrograde transformation dependent on the degree of change of the compression. Different computational retrograde transformation methods are possible for this purpose. For example, it is possible to initially determine the transformation of assigned points in the image (for example of the boundary line bordering the breast) into the corresponding comparison points in the comparison image (thus in the first acquired image) in the computational transformation, and then (assuming this degree of retrograde transformation) to determine the degree of retrograde transformation for all other pixels, etc. A retrograde calculation of the first image data set into the second image data set is also possible.

The computational linking (combination) is then based on approximately identical images of the presented breast, which simplifies the computational linking here.

For example, this computational linking can ensue by forming a difference image data set from the two image data sets and determining a difference image from the difference image data set. This means that the transformed second image or the transformed second image data set is subtracted from the first image or first image data set. Insofar as the tissue is uniformly homogenous, in the ideal case the difference image is contourless to the greatest possible extent because the healthy tissue shifts homogenously and, as a result of the retrograde calculation, ultimately the second image or the second image data set shows or contains the same as the first image or the first image data set. However, if one or more malignant lesions are present that have shifted differently in the deformation due to compression, these are clearly emphasized in a difference operation since, for those malignant lesions, the assumption of a homogenously elastic behavior that forms the basis of the retrograde transformation does not apply, and consequently an actual signal difference within the appertaining pixels occurs in the region of this image section. The subtraction in the framework of the difference image data set generation is only an example; many different calculation formulas or weighting formulas are possible for use in the linking. It is thus possible to unequally weight the two image data sets in the linking in order to ensure that the breast from one image (advantageously the untransformed image) still remains slightly visible in the computationally determined final image to be output, which facilitates orientation for the physician when he or she evaluates the image. The possibility to set parameters for the computational linking (for example by grayscale value windowing or other image processing tools) that accounts for or weights the image contents of the individual image data sets to be linked differently can also be provided to the operator. This means that the operator can make adjustments as needed as to how the computational linking should ensue so that, in the image processing, the processing parameters can be set so that a diagnostically evaluable final image (for example a difference image) is generated.

As already described, the possibility exists to produce the link (for example by different weighting of the image data sets) so that the breast in one image still remains slightly visible. However, it is also possible to link the image data sets such that only the curve of the edge of the mamma shown in one of the two image data sets (in particular in the untransformed image data set) is shown in the image, possibly in a difference image. This also enables the physician to be able to determine the precise location of a possible finding. For example, an edge detection algorithm can be used to determine the edge in the one image data set.

In the implementation of the method according to the invention it is appropriate, for optimal efficiency, for the second degree of compression to be automatically set immediately after acquisition of the first image data set by adjustment of the compression plate, after which the second image data set is immediately acquired and the linking (possibly after prior transformation) subsequently ensues, also followed by the output of the determined image, for example the difference image. The change of the degree of compression can ensue in both directions, meaning that the breast can be compressed more strongly in the acquisition of the first image and be relaxed for the acquisition of the second image, or vice versa. In any case the change leads to an elastic tissue movement from which the acquisition of the elastographic information results.

In addition to the method, the invention also concerns a mammography apparatus having an radiation source, a digital radiation detector, and a support plate and a compression plate between which the breast is compressed while the image is acquired, as well as an image processing device fashioned to implement the described method.

DESCRIPTION OF THE PREFERRED EMBODIMENTS

Figure 1:
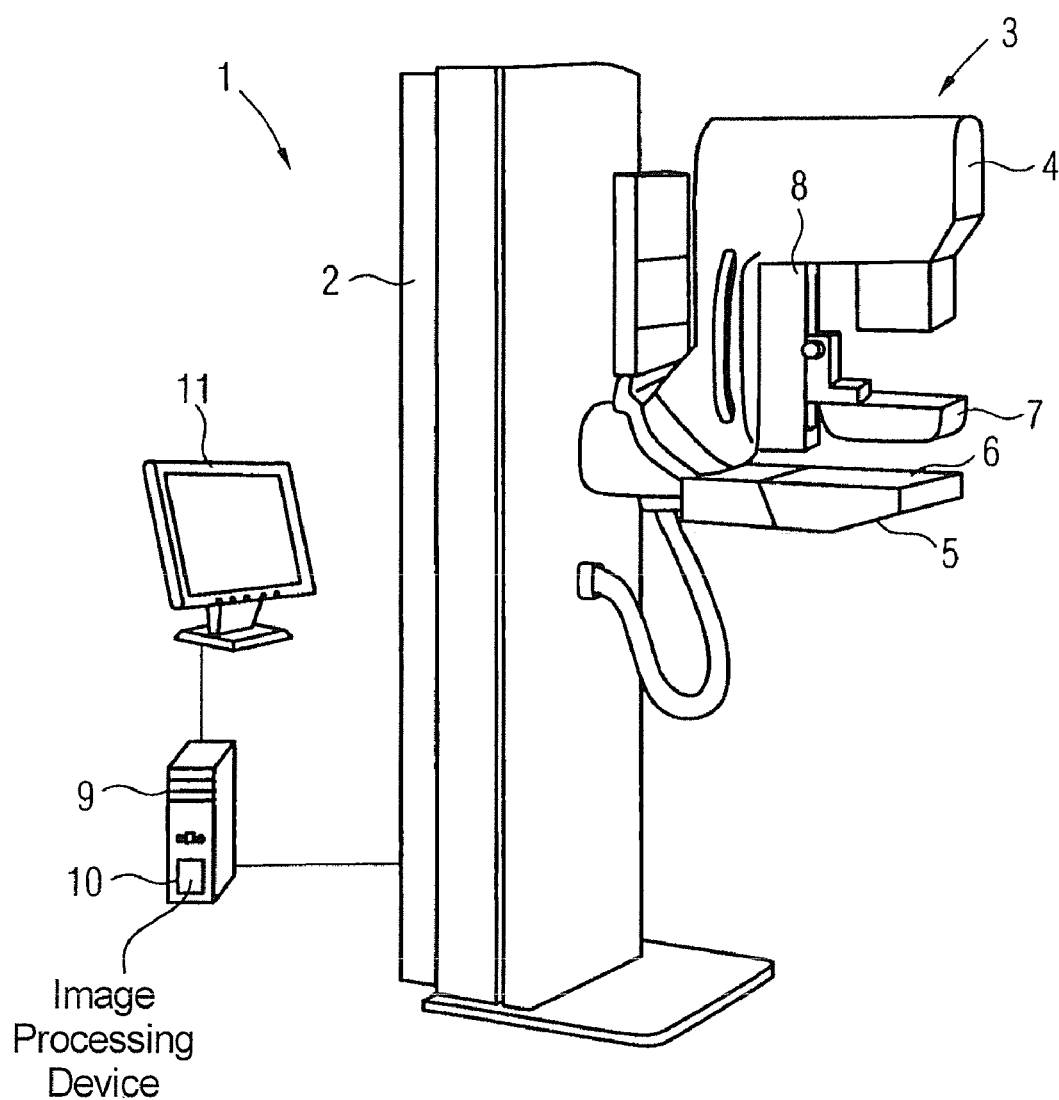
FIG. 1 shows a mammography apparatus.

FIG. 1 shows a known mammography apparatus 1 having a vertical column 2 on which the image acquisition unit 3 is arranged vertically such that it can move. The image acquisition unit 3 has an x-ray source 4 as well as a digital x-ray detector 5 that is arranged below a support plate 6 for the female breast. A compression plate 7 is provided above the support plate 6. The compression plate 7 is likewise vertically driven in an adjustable manner on a vertical support 8. With this compression plate 7 the breast can be compressed in a known manner for image acquisition. A control device 9 is also provided that controls the entire operation of the x-ray apparatus as well as the image acquisition and image evaluation operation, for which a suitable image processing device 10 is provided. Acquired images are output on a monitor 11.

Figure 2:
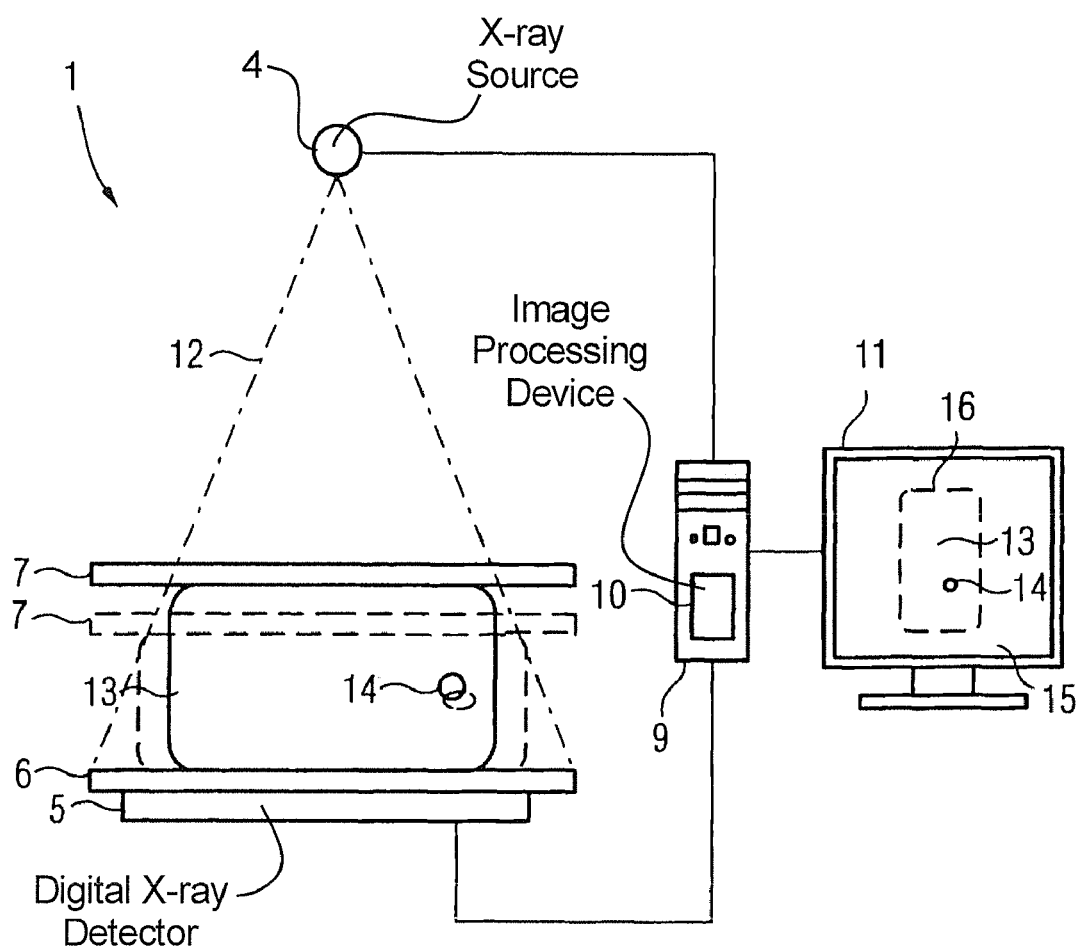
FIG. 2 schematically shows a mammography apparatus of FIG. 1 to explain the method according to the invention.

FIG. 2 shows the mammography apparatus 1 of FIG. 1 in a schematic representation in order to explain the method according to the invention in more detail. The radiation source 4 is shown that emits an x-ray beam (bundle) 12. Also shown is the bearing plate 6 with the radiation detector 5 located underneath as well as the compression plate 7. Furthermore, the breast 13 is shown, that is clearly not presented in its natural shape.

The breast 13 contains a mass 14 which may be a malignant lesion, for example a cancer. The breast 13 is held between the support plate 6 and the compression plate 7 and is compressed between the two. The compression plate can be adjusted by the degree of the vertical displacement of the compression plate 7.

At the beginning of the method, the compression plate 7 is located in a first position that here is shown with solid lines. A first degree of compression of the breast 13 was hereby set. In the first degree of compression, the breast 13 as well as the lesion 14 are likewise shown in solid lines. The radiation beam 12 penetrates the breast 13 in addition to lesion 14; a corresponding image data set that enables the output of a first image is acquired at the radiation detector 5 and stored in the image processing device 10 of the control device 9.

In the second method step, the compression plate 7 is then shifted (displaced)—in the shown example it is moved further back toward the support plate 7, which leads to the situation that the pressure on the breast 13 and the lesion 14 is increased; the mamma 13 is thus inevitably more significantly compressed. This second position of the compression plate 7 is shown in dashed lines; the second degree of compression of the mamma 13 and of the lesion 14 is also shown in dashed lines. This pressure increase or intensification of the compression now leads to the situation that the breast 13 is deformed; this means that it is pressed more significantly and expands laterally in space, as FIG. 2 shows. The variation of the degree of compression likewise leads to a lateral shift of lesion 14. The deformation of the lesion 14 starting from the first degree of compression (where it is thus shown drawn out) to the position as it is shown with dashed lines is strongly dependent on the elastic properties of the lesion. These are distinctly different for benign and malignant lesions. While a benign lesion shows an elastic behavior that approximately corresponds to that of the healthy tissue of the breast 13, a malignant lesion is distinctly harder; it thus behaves distinctly differently in its evasive movement that occurs upon a change of the degree of compression than a benign lesion. If the lesion 14 is a benign lesion, it would lie at a different point than is shown with the dashed lines. The dashed line representation of lesion 14 indicates the position of a malignant lesion.

In each case, a second image data set is now also acquired in the second compression position; the image signals of the radiation detector 5 are in turn stored in the image processing device 10.

The second image data set is then transformed computationally such that the size and location variations occurring due to the elastic deformation are compensated. A retrograde calculation of the image signals to the initial state that the mamma had in the framework of the first image acquisition thus ensues. The second image or the second image data set is thus quasi-transformed into the first image data set. This ensues under the assumption of a homogenous elasticity behavior across the entire area or the entire volume of the breast 13, independent of whether lesions are present or not. However, it also results from this that a malignant lesion 14 is transformed differently or is essentially calculated back into a different starting position upon application of the first degree of compression than actually occurred in the volume. As described, the compression or elasticity behavior of a malignant lesion is different than that of a benign lesion, which exhibits a behavior approximately corresponding to that of healthy tissue.

In the next step, a computational linking of the first, untransformed image data set and the second, transformed image data set is conducted, for example a simple taking of a difference with possible weighting of one image data set. For example, the difference image is calculated as D=A−0.7B, wherein A is the first image data set and B is the transformed second image data set. However, any computational linkings with arbitrary weightings or calculation formulas are possible. The processing can also ensue such that the contours of the breast advantageously starting from the untransformed image data set) are still visible in the difference image, albeit not too clearly, or the edge of the breast is determined, for example via an edge detection algorithm, etc. This is in order to provide the operator with an easier orientation in the difference image.

In any case, the difference image generated in whichever manner or, respectively, the computational link image is then output on the monitor 11 (see FIG. 2) where such a difference image 15 is presented. The still slightly visible edge 16 of the breast 13 is shown on the one hand, as well as the lesion 14 (which clearly emerges in the difference image). The observer thus receives in this way a clearly more specific difference image; compare with the individual image data that the two image data sets yield that were acquired at the different degrees of compression. In these the lesion 14 would be seen only as a slight shadow; it would not be shown clearly and for as long in the image as this is now possible due to the linking according to the invention of the elastography (thus utilization of the different elastic properties of the irradiated tissue) and the radioscopic mammography.

Although modifications and changes may be suggested by those skilled in the art, it is the intention of the inventor to embody within the patent warranted hereon all changes and modifications as reasonably and properly come within the scope of his or her contribution to the art.

I claim as my invention:

1. A method to generate a mammographic image, comprising the steps of:
   placing a breast between a compression plate and a support plate;
   compressing the breast between said compression plate and said support plate with a first degree of compression, and with an x-ray imaging system positioned in an imaging position relative to the breast, irradiating the breast, compressed with said first degree of compression, with x-rays and detecting x-rays attenuated by the breast, with said first degree of compression, to acquire a first image data set;
   compressing the breast between the compression plate and the support plate with a second degree of compression, different from said first degree of compression, and without re-positioning said x-ray imaging system from said imaging position, irradiating the breast compressed with said second degree of compression with x-rays and detecting x-rays attenuated by the breast with said second degree of compression to acquire a second image data set; and
   in a processor, computationally combining said first and second image data sets to generate a diagnostic image data set, representing a diagnostic image of the breast, as an output from said processor.

2. A method as claimed in claim 1 comprising, in said processor before computationally combining said first and second image data sets, transforming one of said first or second image data sets based on an assumption that the breast exhibits homogenous elastic behavior in order to compensate for elastic variation of the breast resulting from said first and second degrees of compression being different from each other.

3. A method as claimed in claim 2 comprising computationally combining said first and second image data by subtracting one of said first or second image data sets from the other of said first or second image data sets to generate difference image data, as said diagnostic image data, and comprising the additional step of generating a difference image, as said diagnostic image, from said difference image data set.

4. A method as claimed in claim 3 comprising forming said difference image data set to cause a curve of an edge of the breast in one of said first or second image data sets to be shown in said difference image.

5. A method as claimed in claim 4 wherein said curve is in said one of said first or second image data sets that is transformed dependent on said homogenous elastic behavior.

6. A method as claimed in claim 4 comprising identifying said edge by executing an edge detection algorithm in said processor.

7. A method as claimed in claim 1 comprising unequally weighting said first and second image data sets when computationally combining said first and second image data sets in said processor.

8. A method as claimed in claim 1 comprising positioning said compression plate at a first position relative to said support plate to produce said first degree of compression, and automatically displacing said compression plate from said first position to a second position relative to said support plate, after acquiring said first image data set, to immediately thereafter acquire said second image data set.

9. A mammography apparatus comprising:
a compression plate and a support plate configured to receive a breast therebetween;
an x-ray radiator and an x-ray detector, both positioned relative to the breast at an imaging position;
said compression plate being operable to compress the breast between said compression plate and said support plate with a first degree of compression and said x-ray radiator being operable to irradiate the breast, compressed with said first degree of compression, with x-rays and said x-ray detector being operable to detect x-rays attenuated by the breast, with said first degree of compression, to acquire a first image data set;
said compression plate being operable to compress the breast between the compression plate and the support plate with a second degree of compression, different from said first degree of compression, and said x-ray radiator being operable, without changing said imaging position, to irradiate the breast compressed with said second degree of compression with x-rays and said x-ray detector being operable to detect x-rays attenuated by the breast with said second degree of compression to acquire a second image data set; and
a processor configured to computationally combine said first and second image data sets to generate a diagnostic image data set, representing a diagnostic image of the breast, as an output from said processor.

10. A mammography apparatus as claimed in claim 9 wherein said processor is configured, before computationally combining said first and second image data sets, to transform one of said first or second image data sets based on an assumption that the breast exhibits homogenous elastic behavior, in order to compensate for elastic variation of the breast resulting from said first and second degrees of compression being different from each other.

11. A mammography apparatus as claimed in claim 10 wherein said processor is configured to computationally combine said first and second image data by subtracting one of said first or second image data sets from the other of said first or second image data sets to generate difference image data, as said diagnostic image data, and to generate a difference image, as said diagnostic image, from said difference image data set.

12. A mammography apparatus as claimed in claim 11 wherein said processor is configured to form said difference image data set to cause a curve of an edge of the breast in one of said first or second image data sets to be shown in said difference image.

13. A mammography apparatus as claimed in claim 12 wherein said curve is in said one of said first or second image data sets that is transformed dependent on said homogenous elastic behavior.

14. A mammography apparatus as claimed in claim 12 wherein said processor is configured to identify said edge by executing an edge detection algorithm in said processor.

15. A mammography apparatus as claimed in claim 9 wherein said processor is configured to unequally weight said first and second image data sets when computationally combining said first and second image data sets.

16. A mammography apparatus as claimed in claim 9 wherein said compression plate is operable to be positioned at a first position relative to said support plate to produce said first degree of compression, and comprising a control unit that automatically displaces said compression plate from said first position to a second position relative to said support plate, after said first image data set is acquired, and that triggers said x-ray radiator to immediately thereafter acquire said second image data set.

* * * * *